(12) United States Patent
Ritter

(10) Patent No.: US 11,601,772 B2
(45) Date of Patent: Mar. 7, 2023

(54) SYSTEMS AND METHODS FOR ENHANCING ATTITUDE AWARENESS IN AMBIGUOUS ENVIRONMENTS

(71) Applicant: Raytheon BBN Technologies Corp., Cambridge, MA (US)

(72) Inventor: Scott E. Ritter, Sudbury, MA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 722 days.

(21) Appl. No.: 16/567,613

(22) Filed: Sep. 11, 2019

(65) Prior Publication Data

US 2020/0166993 A1 May 28, 2020

Related U.S. Application Data

(60) Provisional application No. 62/771,781, filed on Nov. 27, 2018, provisional application No. 62/771,520, filed on Nov. 26, 2018.

(51) Int. Cl.

| H04S 1/00 | (2006.01) |
|---|---|
| G06F 3/01 | (2006.01) |
| H04R 29/00 | (2006.01) |
| G05D 1/00 | (2006.01) |
| G06F 3/16 | (2006.01) |
| A61B 34/35 | (2016.01) |
| H04R 5/033 | (2006.01) |
| H04S 7/00 | (2006.01) |
| G01S 13/50 | (2006.01) |

(Continued)

(52) U.S. Cl.
CPC .............. H04S 1/005 (2013.01); A61B 34/35 (2016.02); G01S 13/505 (2013.01); G05D 1/005 (2013.01); G05D 1/0016 (2013.01);
*G06F 3/012* (2013.01); *G06F 3/167* (2013.01); *H04R 5/033* (2013.01); *H04R 29/001* (2013.01); *H04S 7/304* (2013.01); *A61B 17/3211* (2013.01); *A61B 2017/00128* (2013.01); *H04S 2420/01* (2013.01)

(58) Field of Classification Search
CPC ......... A63G 31/16; G06F 3/012; G06F 3/165; H04N 21/439; H04N 21/41422
USPC ............................................ 701/1, 2, 8, 419
See application file for complete search history.

(56) References Cited

U.S. PATENT DOCUMENTS

| 9,326,058 B2 | 4/2016 | Tachibana et al. |
| 10,596,478 B2 | 3/2020 | Bear et al. |

(Continued)

FOREIGN PATENT DOCUMENTS

| CN | 104395774 | * | 7/2017 | ............ H04W 4/026 |

OTHER PUBLICATIONS

Keshavarz, B., et al. "Vection and visually induced motion sickness: how are they related?" Frontiers in Psychology (2015) vol. 6, Article 472, pp. 1-11.

(Continued)

*Primary Examiner* — Yosef K Laekemariam
(74) *Attorney, Agent, or Firm* — Lando & Anastasi, LLP

(57) ABSTRACT

Systems and methods for using auditorily-induced vection (AIV) to enhance a person's attitude awareness are provided herein. In at least one embodiment, an auditory object is projected based on the orientation of the person or a vehicle and the projected auditory is provided to the person. By projecting the auditory object, the attitude of the person or the vehicle can be conveyed to the person to enhance the person's attitude awareness.

19 Claims, 12 Drawing Sheets

(51) Int. Cl.
*A61B 17/3211* (2006.01)
*A61B 17/00* (2006.01)

(56) References Cited

U.S. PATENT DOCUMENTS

| | | |
|---|---|---|
| 2010/0290636 A1 | 11/2010 | Mao et al. |
| 2012/0262536 A1 | 10/2012 | Chen et al. |
| 2014/0233917 A1 | 8/2014 | Xiang |
| 2015/0048976 A1 | 2/2015 | Petersen et al. |
| 2015/0316577 A1 | 11/2015 | Pakzad et al. |
| 2017/0332186 A1 | 11/2017 | Riggs et al. |
| 2017/0345212 A1 | 11/2017 | Palmieri et al. |
| 2018/0041837 A1 | 2/2018 | Woelfl |
| 2018/0124497 A1 | 5/2018 | Boesen |
| 2018/0221621 A1* | 8/2018 | Kanemaru ............ H04N 21/439 |
| 2018/0228405 A1 | 8/2018 | Burwinkle et al. |
| 2018/0233018 A1 | 8/2018 | Burwinkel et al. |
| 2018/0288558 A1 | 10/2018 | Umminger, III et al. |
| 2019/0215637 A1 | 7/2019 | Lee et al. |
| 2019/0384384 A1 | 12/2019 | Zavesky et al. |

OTHER PUBLICATIONS

Murphy, D., et al. "Spatial sound for computer games and virtual reality," In: M. Grimshaw, ed. 2011. Game Sound Technology and Player Interaction: Concepts and Developments. Hershey PA : Information Science Reference (2011) pp. 287-312.

Valjamae, A., et al. "Auditory landmarks enhance circular vection in multimodal virtual reality," Journal of the Audio Engineering Society (2006) pp. 1-32.

Thibaut Carpentier. Binaural synthesis with the Web Audio API. 1st Web Audio Conference (WAC), Jan. 2015, Paris, France. hal-01247528.

Valjamae, A. "Auditorily-induced illusory self-motion: A review," Brain Research Reviews, 61, (2009) pp. 240-255.

Lackner, J. "Orientation and movement in unusual force environments," Psychological Science (1993) vol. 4, No. 3, pp. 134-142.

International Search Report and Written Opinion of corresponding International Application No. PCT/US2019/061235 dated Feb. 24, 2020.

Ana Tajadura-Jimenez et al: "Principles for Designing Body-Centered Auditory Feedback" In: "The Wiley Handbook of Human Computer Interaction", Dec. 28, 2017 (Dec. 28, 2017), John Wiley & Sons, Ltd, Chichester, UK, XP055665861, ISBN: 978-1-118-97613-5 pp. 371-403, DOI: 10.1002/9781118976005.

* cited by examiner

| Situation | Examples | Impairments | Consequences | Benefits of Solution |
|---|---|---|---|---|
| Teleoperation of vehicles or equipment using first-person display technology | • Drone aircraft piloting<br>• Telerobotic surgical procedures | • No vestibular sense<br>• No touch sense<br>• Loss of visual horizon<br>• No spatial audio | • Reduced operator performance and training rate | Enhanced military, commercial, & medical performance for telepresence |
| • Sensory organ damage or functional deficiency<br>• Expert physical activities by healthy individuals<br>• Activities and events that challenge nominal vestibular organ function | • Meniere's disease<br>• Age-related decline<br>• Multiple Sclerosis<br>• Rock climbing<br>• Low-visibility skydiving<br>• Aircraft operations<br>• Obstacle traversal<br>• Low-visibility aerial troop deployment<br>• Underwater operations<br>• Vestibular organ damage (concussion) | • All senses may be affected | • Increased chance of falls<br>• Decreased mobility<br>• Reduced recovery rates | Reduced medical, insurance, & elder care costs, enhanced mission capabilities & performance |
| Modified or ambiguous gravitational environments | • Orbital freefall (inside spacecraft)<br>• Spacewalks (outside spacecraft)<br>• Fighter piloting<br>• Dynamic underwater operations | • No vestibular sense<br>• Reduced touch sense<br>• Loss of visual horizon<br>• Reduced spatial audio | • Reduced operator performance<br>• Space sickness | Enhanced military, commercial, & medical performance for space-based operations |
| Target localization and coordinated "schooling" behaviors | • Sniper evasion<br>• Stealthy squad deployment, aggregation and orientation | • Reduced visual and audio perception | • Reduced operator performance<br>• Increased danger | Enhanced mission capabilities and squad performance |

FIG. 1

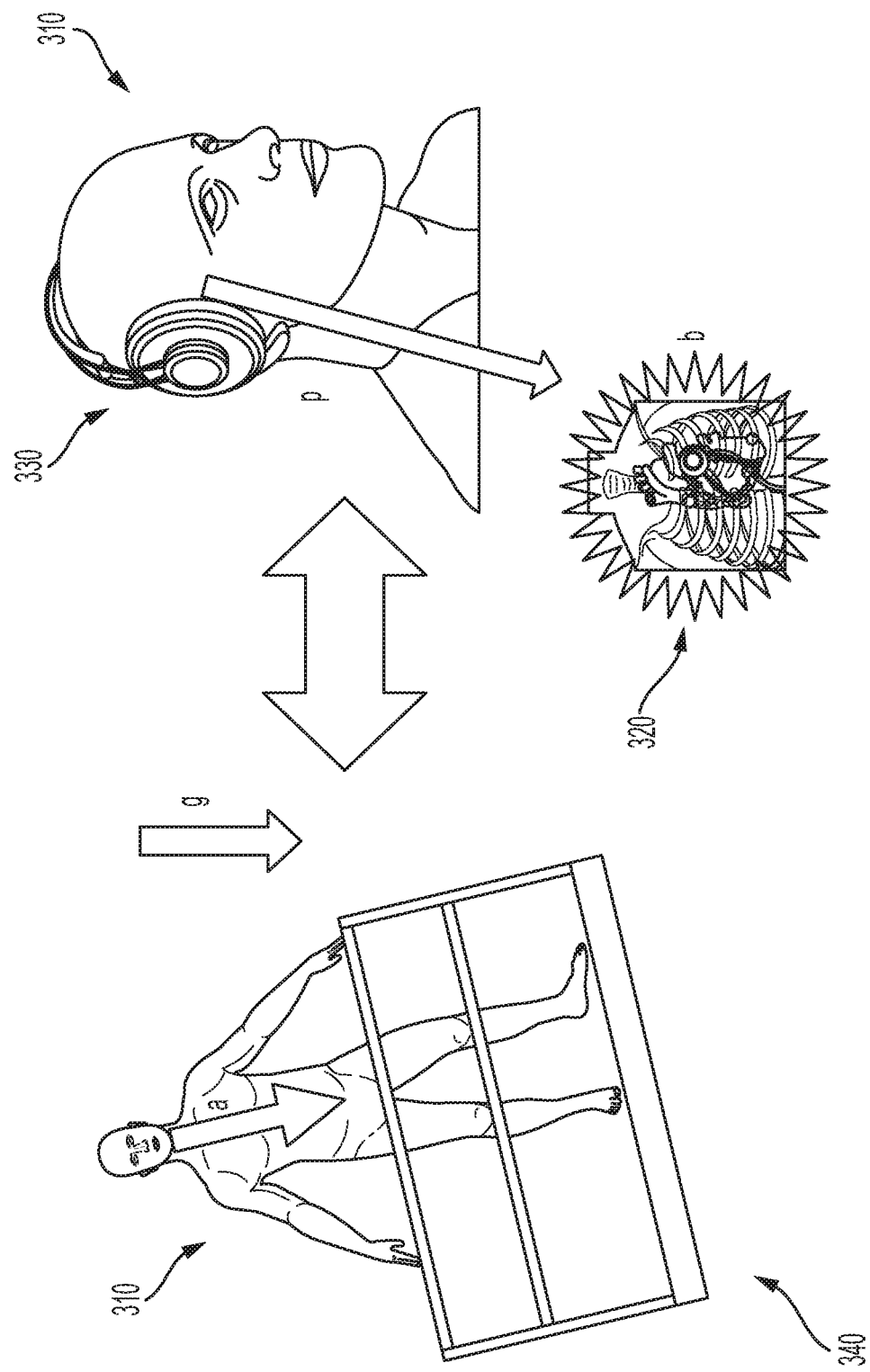

SYSTEMS AND METHODS FOR ENHANCING ATTITUDE AWARENESS IN AMBIGUOUS ENVIRONMENTS

CROSS-REFERENCE TO RELATED APPLICATIONS

This application claims priority to U.S. Provisional Application Ser. No. 62/771,520, titled "ENHANCED ATTITUDE AWARENESS," filed on Nov. 26, 2018, and to U.S. Provisional Application Ser. No. 62/771,781, titled "ENHANCED ATTITUDE AWARENESS," filed on Nov. 27, 2018, both of which are incorporated herein by reference in their entirety.

BACKGROUND

People rely primarily on the vestibular organs of the inner ear to sense their attitude (e.g., to orient and stabilize themselves while walking along a corridor without falling over). In cases of reduced or absent vestibular function, people compensate with increased reliance on vision, touch (including proprioception) and hearing.

SUMMARY

At least one aspect of the invention is directed to a method of using auditorily-induced vection (AIV) to provide an operator of a remote vehicle with an enhanced sense of the remote vehicle's attitude. The method includes obtaining an auditory object associated with the remote vehicle, determining an orientation of the remote vehicle, projecting the auditory object relative to the orientation of the remote vehicle, and providing the projected auditory object to the operator to convey the attitude of the remote vehicle.

In one embodiment, the method includes transmitting at least one of the auditory object and the orientation of the remote vehicle from the remote vehicle. In some embodiments, the method includes receiving at least one of the auditory object and the orientation of the remote vehicle transmitted from the remote vehicle.

In certain embodiments, determining the orientation of the remote vehicle includes determining an orientation vector relative to a reference vector. In some embodiments, projecting the auditory object relative to the orientation of the remote vehicle includes determining a projection source location based on the orientation vector. In one embodiment, the projection source location is a point in space about the operator's head.

In some embodiments, projecting the auditory object includes applying a head-related transfer function (HRTF) corresponding to the projection source location to the auditory object. In one embodiment, the HRTF represents a characterization of how the operator hears sound from the projection source location. In certain embodiments, providing the projected auditory object to the operator includes indicating a deviation of the orientation vector from the reference vector. In one embodiment, the method includes modifying the projected auditory object to enhance the operator's perception of the deviation of the orientation vector from the reference vector. In some embodiments, the reference vector is a gravity vector. In certain embodiments, the auditory object is an engine sound.

According to another aspect of the invention, an auditorily-induced vection (AIV) system for assisting an operator of a remote vehicle is provided. The system includes at least one acoustic sensor configured to sense an auditory object associated with the remote vehicle, at least one attitude sensor configured to sense an orientation of the remote vehicle, at least one transmitter configured to transmit the auditory object and the orientation of the remote vehicle, and a controller including at least one receiver, the controller configured to: receive the auditory object from the at least one transmitter, receive the orientation of the remote vehicle from the at least one transmitter, project the auditory object relative to the orientation of the remote vehicle, and provide the projected auditory object to earphones to convey the attitude of the remote vehicle to the operator.

In one embodiment, the system includes a memory device coupled to the controller, the memory device configured to store a plurality of points in space about the operator's head and a head-related transfer function (HRTF) corresponding to each of the plurality of points. In some embodiments, each HRTF represents a characterization of how the user hears sound from each of the plurality of points.

In certain embodiments, the controller is configured to determine a projection source location relative to the orientation of the remote vehicle. In one embodiment, wherein projecting the auditory object the controller is configured to select a point from the plurality of points based on the projection source location and apply the corresponding HRTF to the auditory object. In another embodiment, wherein in projecting the auditory object the controller is configured to select two or more points from the plurality of points based on the projection source location, interpolate an HRTF using the HRTFs corresponding to the two or more selected points, and apply the interpolated HRTF to the auditory object.

In some embodiments, the controller is configured to modify the projected auditory object to enhance a non-level attitude perception. In one embodiment, wherein in modifying the projected auditory object the controller is configured to make the projected auditory object louder as the remote vehicle approaches a boundary. In some embodiments, the controller is configured to apply a Doppler shift to the auditory object to enhance the operator's awareness of the remote vehicle's velocity. In certain embodiments, the remote vehicle is one of a drone or a teleoperated scalpel.

At least one aspect of the invention is directed to a method of using auditorily-induced vection (AIV) to provide a user with an enhanced sense of attitude. The method includes obtaining an auditory object associated with the user, determining an orientation of the user, projecting the auditory object relative to the orientation of the user, and providing the projected auditory object to the user to convey the user's attitude.

In one embodiment, determining the orientation of the user includes determining an orientation vector relative to a reference vector. In some embodiments, projecting the auditory object relative to the orientation of the user includes determining a projection source location based on the orientation vector. In certain embodiments, the projection source location is a point in space about the user's head.

In some embodiments, projecting the auditory object includes applying a head-related transfer function (HRTF) corresponding to the projection source location to the auditory object. In certain embodiments, the HRTF represents a characterization of how the user hears sound from the projection source location. In one embodiment, providing the projected auditory object to the user includes indicating a deviation of the orientation vector from the reference vector. In some embodiments, the method includes modifying the projected auditory object to enhance the user's perception of the deviation of the orientation vector from the reference vector. In certain embodiments, the reference vector is a gravity vector.

In one embodiment, the orientation of the user corresponds to a first sense of motion in a first direction and the projected auditory object provides a second sense of motion in a second direction to the user. In certain embodiments, the second sense of motion offsets the first sense of motion. In some embodiments, the auditory object includes sound of one of the user's breath, heartbeat, and blood flow.

According to another aspect of the invention, an auditorily-induced vection (AIV) system for providing a user with an enhanced sense of attitude is provided. The system includes at least one acoustic sensor configured to sense an auditory object associated with the user, at least one attitude sensor configured to sense an orientation of the user, and a controller configured to receive the auditory object from the at least one acoustic sensor, receive the orientation of the user from the at least one attitude sensor, project the auditory object relative to the orientation of the user, and provide the projected auditory object to earphones to convey the user's attitude.

In some embodiments, the system includes a memory device coupled to the controller, the memory device configured to store a plurality of points in space about the user's head and a head-related transfer function (HRTF) corresponding to each of the plurality of points. In certain embodiments, the controller is further configured to determine a projection source location relative to the orientation of the user.

In one embodiment, wherein projecting the auditory object the controller is configured to select a point from the plurality of points based on the projection source location and apply the corresponding HRTF to the auditory object. In another embodiment, wherein in projecting the auditory object the controller is further configured to select two or more points from the plurality of points based on the projection source location, interpolate an HRTF using the HRTFs corresponding to the two or more selected points, and apply the interpolated HRTF to the auditory object.

In some embodiments, the controller is configured to modify the projected auditory object to enhance a non-level attitude perception. In one embodiment, wherein in modifying the projected auditory object the controller is configured to make the projected auditory object louder to enhance the non-level attitude perception. In certain embodiments, wherein in modifying the projected auditory object the controller is configured to exaggerate a projection angle of the projected auditory object to enhance the non-level attitude perception.

At least one aspect of the invention is directed to a method of using auditorily-induced vection (AIV) to provide a user with a sense of direction in a non-gravitational environment. The method includes determining a reference point within the environment, obtaining an auditory object associated with the user, determining an orientation of the user, projecting the auditory object based on the orientation of the user, and providing the projected auditory object to the user to convey the user's orientation relative to the reference point.

In one embodiment, determining the reference point includes determining a reference vector. In some embodiments, determining the orientation of the user includes determining an orientation vector relative to the reference vector. In certain embodiments, projecting the auditory object based on the orientation of the user includes determining a projection source location based on the orientation vector. In one embodiment, the projection source location is a point in space about the user's head.

In some embodiments, projecting the auditory object includes applying a head-related transfer function (HRTF) corresponding to the projection source location to the auditory object. In certain embodiments, the HRTF represents a characterization of how the user hears sound from the projection source location. In certain embodiments, providing the projected auditory object to the user includes indicating a deviation of the orientation vector from the reference vector. In one embodiment, the method includes modifying the projected auditory object to enhance the user's perception of the deviation of the orientation vector from the reference vector. In some embodiments, the auditory object includes sound of one of the user's breath, heartbeat, and blood flow.

According to another aspect of the invention, an auditorily-induced vection (AIV) system for providing a user with an enhanced sense of direction in a non-gravitational environment is provided. The system includes at least one acoustic sensor configured to sense an auditory object associated with the user, at least one attitude sensor configured to sense an orientation of the user, and a controller configured to: receive the auditory object from the at least one acoustic sensor, receive the orientation of the user from the at least one attitude sensor, project the auditory object based on the orientation of the user and a reference point, and provide the projected auditory object to earphones to convey the user's orientation relative to the reference point.

In some embodiments, the system includes a memory device coupled to the controller, the memory device configured to store a plurality of points in space about the user's head and a head-related transfer function (HRTF) corresponding to each of the plurality of points. In certain embodiments, the controller is configured to determine a projection source location based on the orientation of the user and the reference point.

In one embodiment, wherein in projecting the auditory object the controller is configured to select a point from the plurality of points based on the projection source location and apply the corresponding HRTF to the auditory object. In another embodiment, wherein in projecting the auditory object the controller is configured to select two or more points from the plurality of points based on the projection source location, interpolate an HRTF using the HRTFs corresponding to the two or more selected points, and apply the interpolated HRTF to the auditory object.

In some embodiments, the controller is configured to modify the projected auditory object to enhance a non-level attitude perception. In certain embodiments, wherein in modifying the projected auditory object the controller is further configured to make the projected auditory object louder to enhance the non-level attitude perception. In one embodiment, wherein in modifying the projected auditory object the controller is further configured to exaggerate a projection angle of the projected auditory object to enhance the non-level attitude perception. In some embodiments, the controller is configured to apply a Doppler shift to the auditory object to indicate a rate of change of the at least one user's orientation. In certain embodiments, the reference point is a location associated with a spacecraft.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 1 is a table presenting some examples of situations in which a person may experience impaired attitude awareness;

FIGS. 5A and 5B are diagrams conceptually illustrating the use of AIV to offset a sense of vehicle motion;

DETAILED DESCRIPTION

Figure 2:
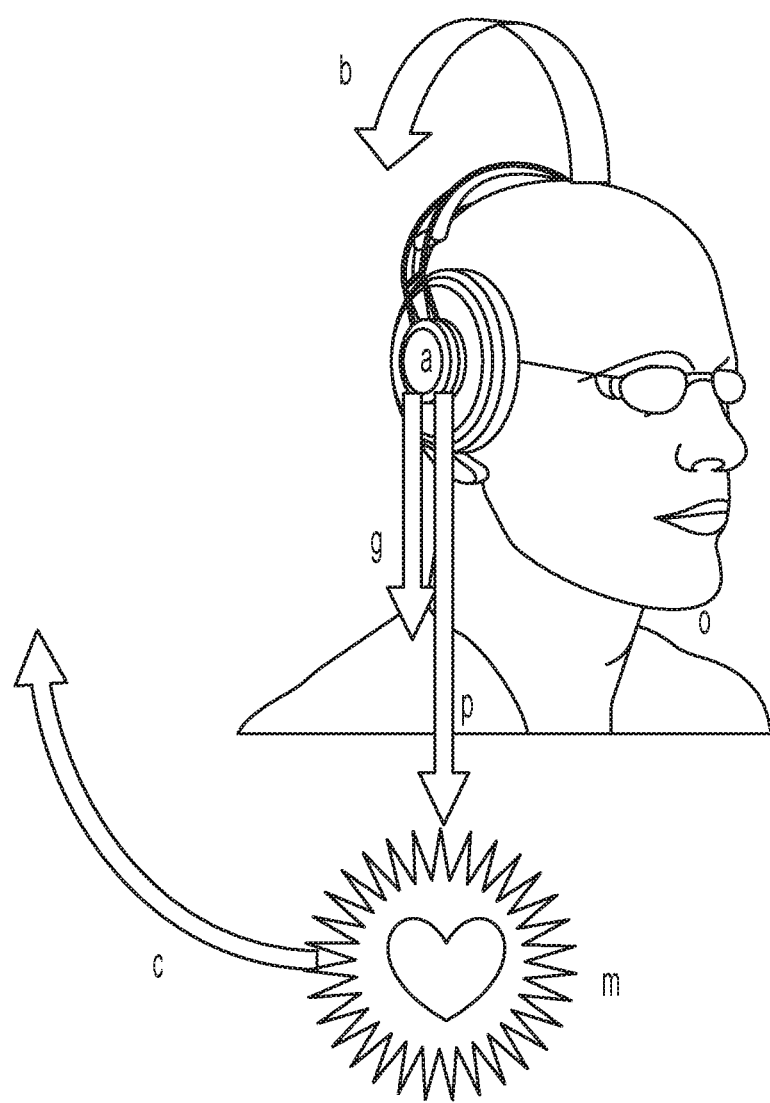
FIG. 2 is a diagram showing an example of the use of auditorily induced vection (AIV)

There exists a wide variety of scenarios and circumstances in which people experience reduced attitude awareness, or impairments in their attitude awareness. This can be the result of physical impairments or due to the environment in which the person is operating. For example, as the quantity, quality, and timeliness of battlefield information made available to the individual soldier have increased, the means to disseminate and make that information actionable have become ever more critical; however, present-day information interfaces, developed to facilitate information access, typically subjugate a soldier's visual awareness and threaten to overwhelm his attention. In another example, while teleoperating a remote vehicle, operators typically rely on first-person display technology to determine how the vehicle should be controlled. As such, an operator is typically provided with minimal feedback and awareness of the remote vehicle's orientation, limiting the operator's ability to control the remote vehicle accurately. Table 1 presented in FIG. 1. provides additional examples of various situations in which a person may experience impaired attitude awareness, and the potential benefits of providing a corresponding solution.

Aspects and embodiments described herein are directed to methods and apparatus to augment attitude awareness and compensate for impairments. In particular, certain aspects and embodiments provide a compact, nonintrusive mechanism that leverages vection (the induced illusion of self-motion) and real-time digital audio processing to provide continuous informational awareness for soldiers or other users in terms of, for example, "which way?" and "how much, how critical, or how far?" Embodiments of the solutions disclosed herein are feasible, both technically and financially (e.g., affordable to develop and deploy), physiologically non-invasive and non-encumbering, and logistically compatible with existing platforms.

Vector fields can be used to represent critical information that is common among teams on the battlefield as well as in a variety of other situations. With good awareness of the representative vector field, the location and magnitude of any respective feature are immediately accessible. Intrinsic to humans are the vestibular organs, with which we sense the acceleration vector field, including the Earth's gravitational vector, g. Changes in acceleration are perceived as self-motion. Vision and hearing work synergistically with vestibular senses to provide body orientation awareness relative to g. Studies have demonstrated that auditory stimuli can induce and affect vection. The induced illusion of self-motion by auditory means is called auditorily-induced vection (AIV). AIV may have both circular (angular) and linear components.

Aspects and embodiments described herein are directed to using AIV to provide a sense of direction or directional motion to enhance a person's attitude awareness in environments in which the person would otherwise have reduced or impaired attitude awareness. Certain embodiments leverage the low-cost availability of compact, sensitive micro-electro-mechanical systems (MEMS) transducers, dense, low-power processors and field-programmable gate arrays (FPGAs), and high-energy-density batteries with efficient power delivery systems to provide a practical, wearable device that can combine g or other vectors with outputs from existing systems or other environmental features and map the results onto auditory objects with sufficiently low latency to produce AIV. The resulting effect can provide or enhance awareness of those features without encumbering the user's visual field. In addition, there may be synergistic vection effects when the auditory stimuli are combined with other sensory modalities (e.g., vision or touch) and/or derived in accordance with conceptual references (e.g., stationary and dynamic ecological sounds, such as water fountains, cars, etc.). As an additional benefit, in certain embodiments, the same device can also map non-vection-related features such as threat locations onto the user's aural awareness.

Aspects and embodiments described herein use externally-captured reference signals (e.g., engine sounds or body sounds, such as heartbeats or breaths) or internally-synthesized signals (e.g., modulated pink noise or chirps) to represent ecological auditory references. Embodiments of the system then apply effects (e.g., pitch shift or gain) to these signals to impose additional information upon them. Embodiments of the system then apply head-related transfer functions (HRTFs) to spatially situate or project the resulting signal with respect to the operator. The apparent location of the sound is controlled by the vector corresponding to the particular feature represented.

An example is vestibular augmentation to enhance an operator's balance in disorienting environments and is illustrated in FIG. 2. In this example, the operator's own heartbeat and breath sound (m) are both attenuated and doppler-shifted downward to indicate increasing altitude above ground to the operator (o), regardless of his or her orientation. The modified reference sound can be projected anywhere onto an imaginary sphere about the operator. In certain examples, the sound is projected in the direction of g, as sensed by a head-mounted accelerometer integrated into the earphones (a). When the operator's head is in an upright and level orientation, the sound is perceived immediately below him (p). If the operator's head were to lean right (b), then the reference sound may correspondingly sweep upward from below the him in an arc toward his right side, as indicated by the purple arrow (c). In addition, a nonlinear relationship between head angle from normal and p can be imposed to exaggerate any impending loss of balance. The resulting AIV, particularly when combined with other sensory modalities (e.g., haptic pressure, proprioception, and vision), may enable the operator to outperform users without AIV technology.

Various examples of applying AIV to provide enhanced attitude awareness are discussed in more detail below.

As discussed above, head-related transfer functions (HRTF's), and real-time signal and sensor processing can be used to project a stationary auditory object relative to a subject. This auditory projection is used to cause auditorily induced vection to provide the subject with a sense of direction or enhanced attitude awareness. According to certain embodiments, synthetic Doppler effect and acoustic parallax can be used to induce or enhance linear vection components.

A head-related transfer function (HRTF) characterizes how an ear receives a sound from a point in space. As sound strikes the subject, the size and shape of the head, ears, and ear canal, the density of the head, and the size and shape of nasal and oral cavities, all transform the sound and affect how it is perceived, boosting some frequencies and attenuating others. The HRTF describes how a sound from a specific point in space arrives at the ear (generally at the outer end of the auditory canal) and is heard by the subject. Thus, a pair of HRTFs for two ears can be used to synthesize a binaural sound that seems to come from a particular point in space. Although humans have only two ears, sounds can be located in three dimensions (range or distance and direction above and below, in front and to the rear, and to either side) because the brain, inner ear and the external ears (pinna) work together to make inferences about location.

Humans estimate the location of a source by taking cues derived from one ear (monaural cues), and by comparing cues received at both ears (difference cues or binaural cues). Among the difference cues are time differences of arrival and intensity differences. The monaural cues come from the interaction between the sound source and the human anatomy, in which the original source sound is modified before it enters the ear canal for processing by the auditory system. These modifications encode the source location, and may be captured via an impulse response which relates the source location and the ear location. This impulse response is termed the head-related impulse response (HRIR). Convolution of an arbitrary source sound with the HRIR converts the sound to that which would have been heard by the listener if it had been played at the source location, with the listener's ear at the receiver location. The HRTF is the Fourier transform of HRIR. Thus, the HRTF from a given source location can be obtained by measuring the corresponding HRIR, h(t), at the ear drum for an impulse function $\Delta(t)$ placed at the source location (e.g., using one or more sensors), and taking the Fourier transform of the HRIR. The measurements can be repeated to obtain an array of HRTFs corresponding to many different points in space around the subject.

Using the HRTF, a "virtual auditory space" surrounding a subject wearing headphones can be created based on the assumption that if the acoustical waveforms present at the subject's eardrums are the same whether coming from the headphones or from free space, then the subject's listening experience should be the same. Generally, sounds generated from headphones appear to originate from inside the head. Using the HRTF, the headphones can instead spatially position the sound in the virtual auditory space surrounding the subject's head. By filtering a sound by the HRTF corresponding to a specific location in space (e.g., directly behind the subject, to the right of the subject, or directly below the subject), the sound can be made to appear to the subject as though it were coming from that location in space, even though in reality, the sound is produced through the headphones worn by the subject.

A specific HRTF is unique to each person, due to its dependence on physical characteristics of the person (e.g., size and shape of parts of the ears, etc.); however, a generalized HRTF can be used with acceptable accuracy to create the virtual auditory space for most users. For example, the HRIRs for a "dummy head" of idealized geometry can be measured, and the corresponding HRTFs calculated to produce an array of generalized HRTFs. These generalized HRTFs can be used to filter sounds so as to position the sounds at specific points in the virtual auditory space around a user. This approach may be significantly less expensive and more versatile than creating an array of user-specific HRTFs for individual operators.

According to certain embodiments described herein, auditorily induced vection (AIV) is achieved by using the HRTFs to position a certain sound or sounds at a specific perceived location relative to a user, and by controlling characteristics of the sound(s), such as volume, for example. The AIV can be applied to enhance the user's attitude awareness, for example by providing a sense of direction or directional motion, such as a perceived sense of gravity.

Certain embodiments described herein are directed to providing enhanced auditorily induced vection for telepresence. For example, AIV can be applied to provide the operator of a remote vehicle, such as a drone, with an enhanced sense of the attitude of the remote vehicle to assist the operator in piloting the vehicle. Similarly, AIV can be used to assist an operator of a remote tool (e.g., teleoperated scalpel) or other device.

Figure 3A:
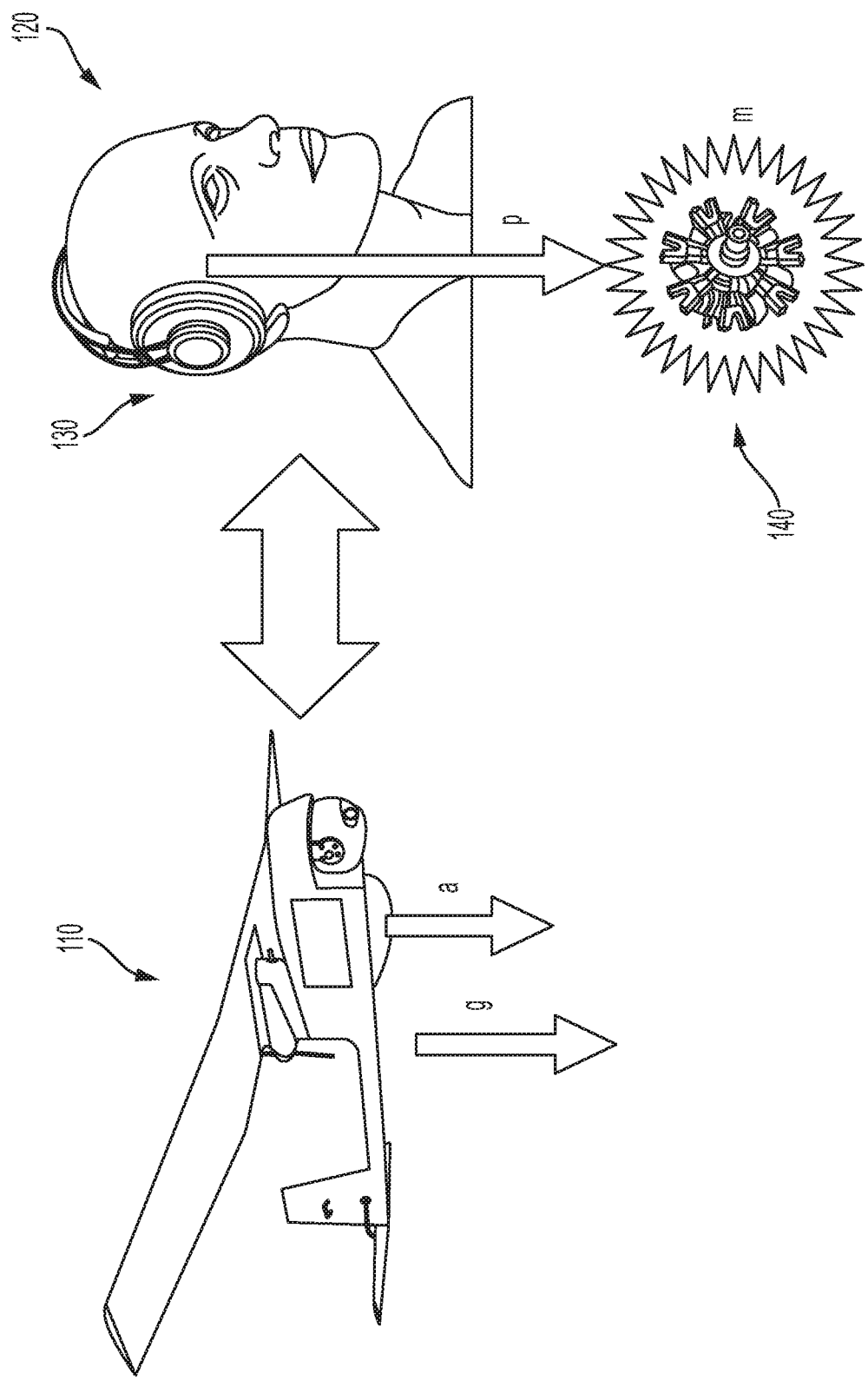
FIGS. 3A and 3B are diagrams conceptually illustrating the use of AIV to assist in remote operation of a vehicle, tool, or other device.
Figure 3B:
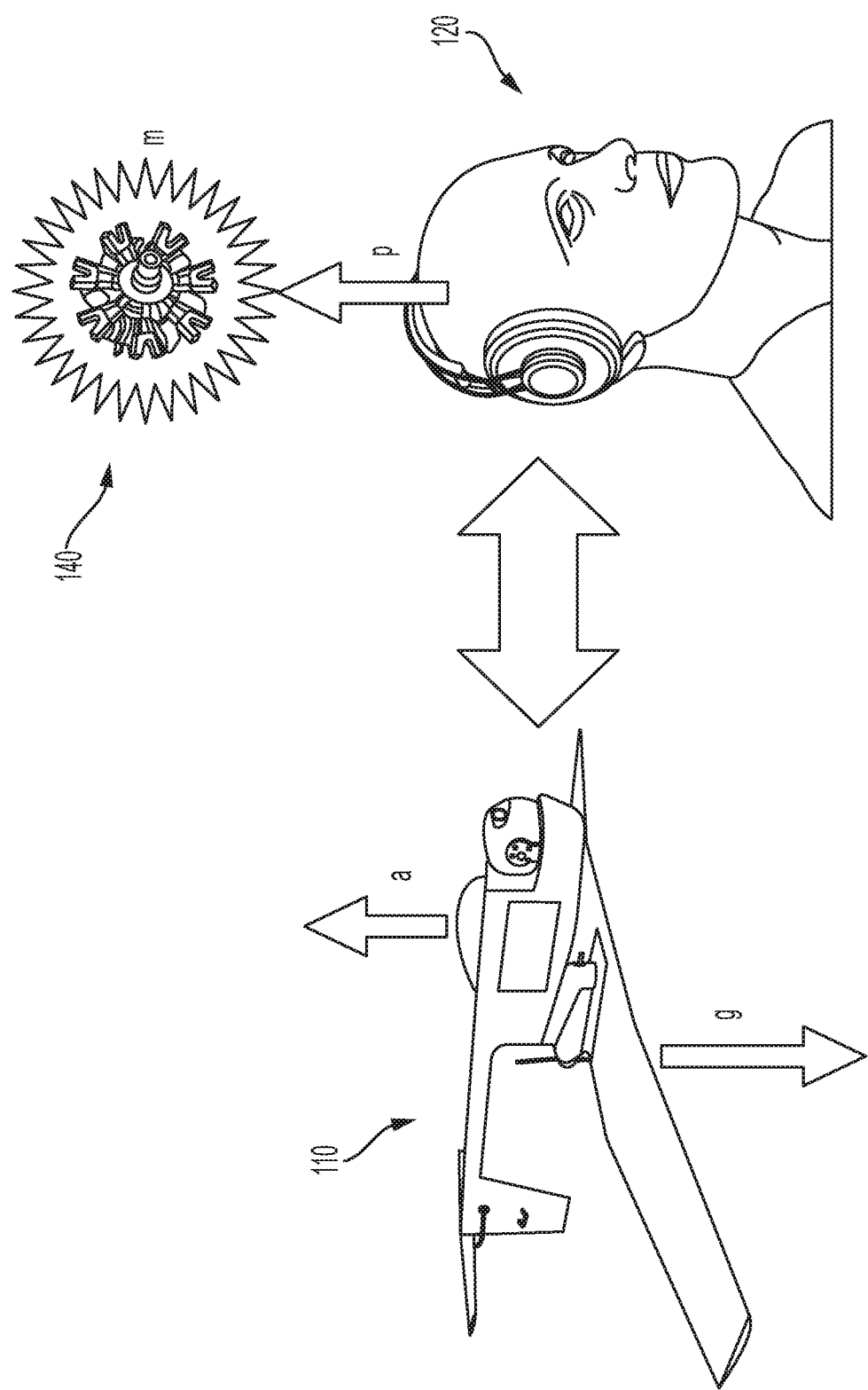

FIGS. 3A and 3B illustrate an example of a telepresence application of AIV according to certain embodiments described herein. In this example, the remote vehicle 110 is a remote aircraft, such as a drone, but those skilled in the art will appreciate, given the benefit of this disclosure, that the principles disclosed herein can be applied equally to other remote vehicles, tools, or devices. The orientation of the remote vehicle 110 can be sensed using vehicle-local sensors, such as a MEMS gyroscope and/or one or more accelerometers. Alternately, other sensors (e.g., video), either local to or in the vicinity of the remote vehicle or tool may be used. In one example, it may be relevant to an operator 120 to know the orientation of the remote vehicle 110 relative to a gravity vector, g. For example, the operator 120 may need to fly the remote vehicle 110 on a very level plane, and therefore any deviation relative to the gravity vector g (i.e., if the attitude of the remote vehicle 110 changes such that it is flying slightly upward or slightly downward instead of level) may be communicated to the operator 120 via AIV. A vector, a, representative of the orientation of the remote vehicle 110 may be provided to the operator 120. An ecological auditory object 140 (e.g., actual vehicle engine sound m) may be projected through earphones or headphones 130 worn by the operator 120 to indicate the g vector (gravity) to the operator 120. Through the use of the HRTF, as discussed above, the operator 120 hears the motor sound m at a projection vector p to convey the vehicle orientation a. Nominally, p is projected onto a virtual sphere (not shown) about the operator's head. In the illustrated example, when the remote vehicle 110 is level with respect to the gravity vector g, the motor sound m is projected directly below the operator 120, as shown in FIG. 3A. When the remote vehicle 110 is inverted, as shown in FIG. 3B, the sound may be projected directly above the operator 120.

In another example, when the remote vehicle 110 turns or rolls with respect to the gravity vector g, the motor sound m can be projected to simulate a shift relative to gravity that the operator 120 would feel from within the remote vehicle 110. For example, when the remote vehicle 110 rolls left, the motor sound m may be projected from the right side of the operator 120, simulating the effect of the operator 120 shifting with respect to the gravity vector g.

In certain examples, the shape and symmetry of the projection sphere can be modified to carry additional information or to enhance perceived deviation from g. For example, the projection sphere radius may be made proportional to altitude and represented by amplitude. The sound m can be made louder the closer the remote vehicle 110 is to the ground, for example. In one example the angle of p may be exponentially exaggerated to enhance non-level attitude perception. The rate of change of the projection sphere radius (linear translation) may be enhanced with synthesized Doppler shift to enhance awareness of the velocity of the remote vehicle 110. In some examples, the ecological auditory object 140 (e.g., motor sound m) may be collected using acoustic sensors; however, in other examples, the ecological auditory object 140 may be synthesized. For example, the ecological auditory object 140 may be synthesized based on an operational parameter of the remote vehicle 110 (e.g., velocity).

Certain embodiments described herein are directed to using AIV with a vestibular prosthesis. The vestibular system is the sensory system that provides the leading contribution to the sense of balance and spatial orientation for the purpose of coordinating movement with balance. The vestibular system sends signals primarily to the neural structures that control eye movements, and to the muscles that keep a person (or animal) upright and in general control of posture. The projections to the former provide the anatomical basis of the vestibulo-ocular reflex, which is required for clear vision, while the projections to the latter provide the anatomical means required to enable the person to maintain his or her desired position in space. The brain uses information from the vestibular system in the head and from proprioception throughout the body to enable the person to understand his or her body's dynamics and kinematics (including its position and acceleration) from moment to moment. Experience from the vestibular system is called equilibrioception, and is used to provide a sense of balance and for spatial orientation. When the vestibular system is stimulated without any other inputs, one experiences a sense of self-motion. For example, a person sitting on a chair in complete darkness will feel that he or she has turned to the left if the chair is turned to the left. Similarly, a person in an elevator may feel that he or she is descending as the elevator starts to descend. There are a variety of direct and indirect vestibular stimuli which can make people feel they are moving or tilted when they are not, or vice versa. Accordingly, in certain embodiments, AIV can be used to apply vestibular stimuli to enhance a person's perception of orientation and/or motion and provide improved attitude awareness.

Figure 4A:
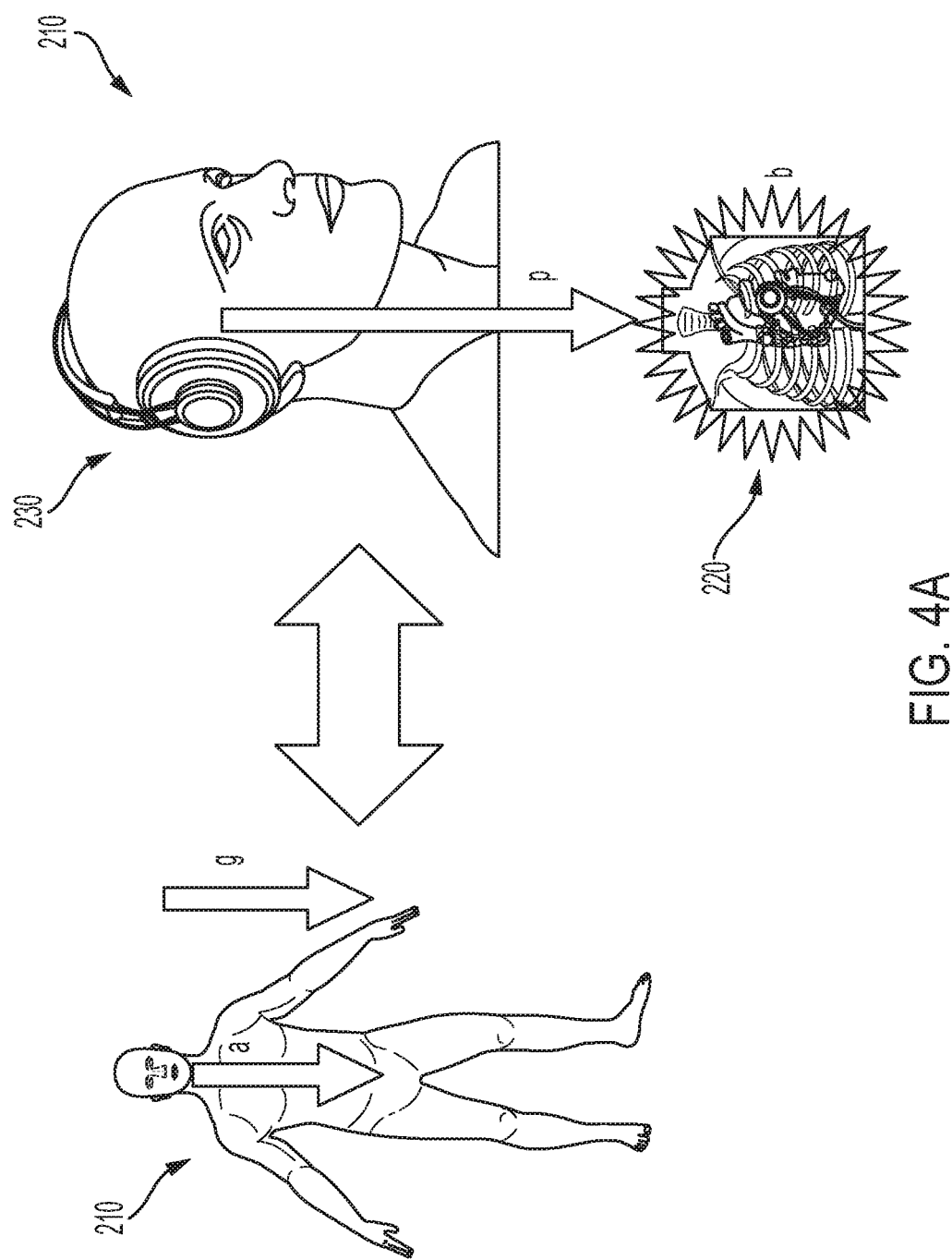
FIGS. 4A and 4B are diagrams conceptually illustrating the use of a vestibular prosthesis including AIV.
Figure 4B:
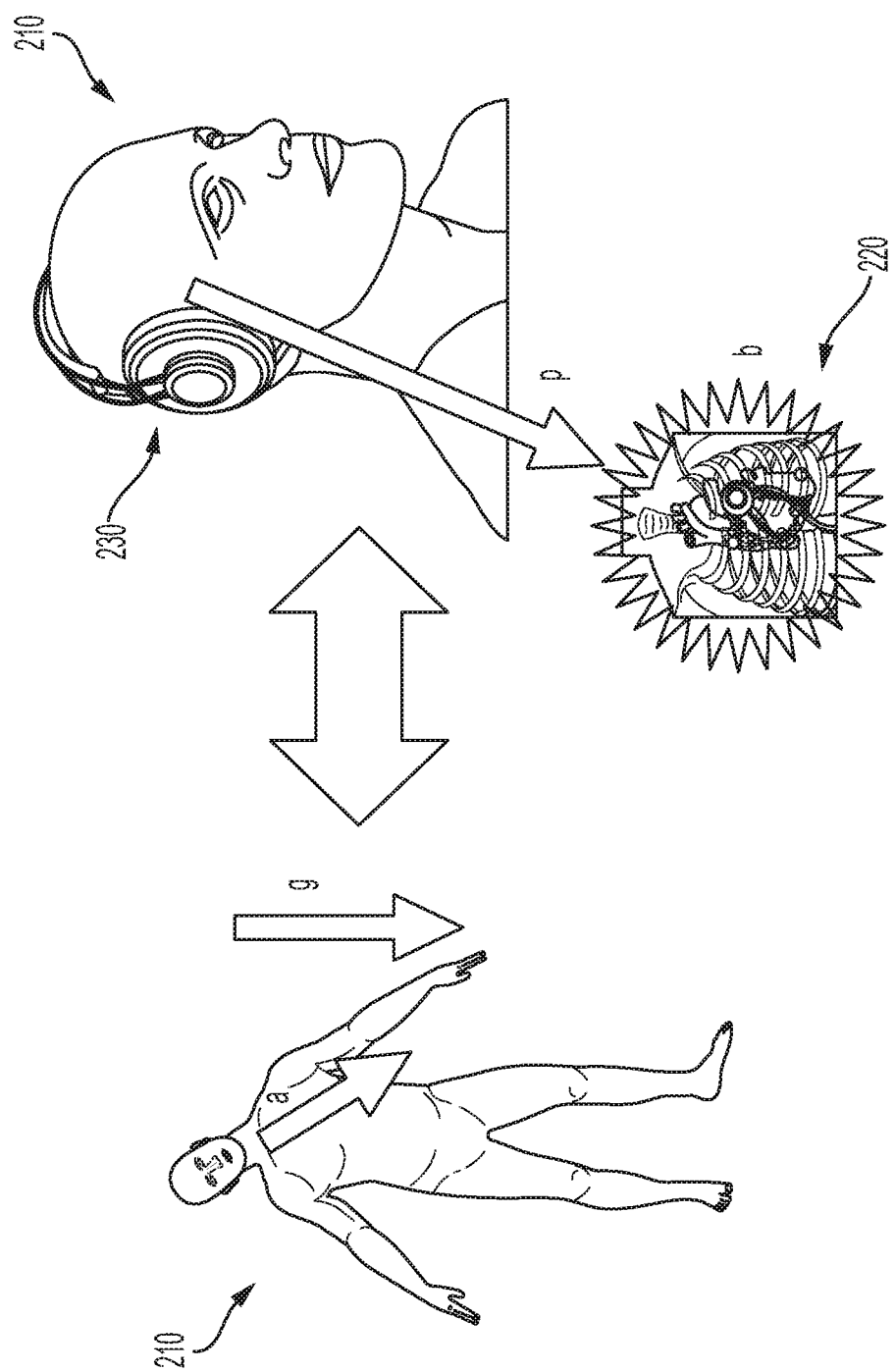

FIGS. 4A and 4B illustrate an example of a vestibular prosthesis application of AIV according to certain embodiments described herein. Similar to the telepresence example discussed above, in this example, the orientation of a patient or subject 210 can be sensed using body-local sensors, such as a MEMS gyroscope and/or accelerometer(s). The sensor(s) can be mounted or worn on the subject's head, torso, or other body part(s). For example, earphone-mounted sensors may be used. Alternately, other sensors (e.g., video), either local to or in the vicinity of the subject 210 may be used; however, these may be less preferred in some applications than a compact and self-contained approach using only body-local sensors. The sensors sense the orientation of the subject 210 (a vector) relative to gravity (g vector). An ecological auditory object 220 (e.g., a body sound, b, such as the sound of the subject's breath, heartbeat, or blood flow) is projected to indicate the g vector (gravity) to the subject 210 via headphones 230. In some examples, the prosthesis can include one or more sensors to sense local body sounds (b) from the subject 210, and those sounds can be projected as the auditory object 220. In other examples, the auditory object 220 can include synthesized or generated sounds that may or may not correspond or be similar to a local body sound of the subject 210. As discussed above, the subject hears the body sounds or other sounds at a projection vector p that conveys the a vector. Nominally, p is projected onto a virtual sphere (not shown) about the head of the subject 210. When the subject 210, or a certain body part of the subject 210, tilts relative to the gravity vector g, the sound(s) 220 are projected accordingly. For example, when the subject's head attitude is canted relative to g, the body sounds b can be projected accordingly, as shown in FIG. 4B.

In certain examples the projection sphere shape and symmetry can be modified to carry additional information or enhance perceived deviations from g. For example, the angle of p may be exponentially exaggerated to enhance non-level attitude perception. In addition, the gain of p (e.g., the volume of the projected sound 220) may be increased to enhance non-level attitude perception. In certain examples, the angle of p may be combined with supplementary local sensors (e.g., shoe-mounted pressure sensors) to enhance subject attitude self-correction. In some examples, the ecological auditory object 220 may be collected using acoustic sensors; however, in other examples, the ecological auditory object 220 may be synthesized.

Certain embodiments are directed to using enhanced auditorily induced vection to offset a sense of motion. For example, when traveling on or within a vehicle (e.g., boat, spacecraft, etc.), a person's vestibular system may be disturbed by the vehicle's motion. Such disturbances may result in what is commonly referred to as motion sickness. In one example, AIV may be used to provide a person with a sense of motion that offsets the vehicle's motion, preventing or alleviating motion sickness.

Figure 5A:
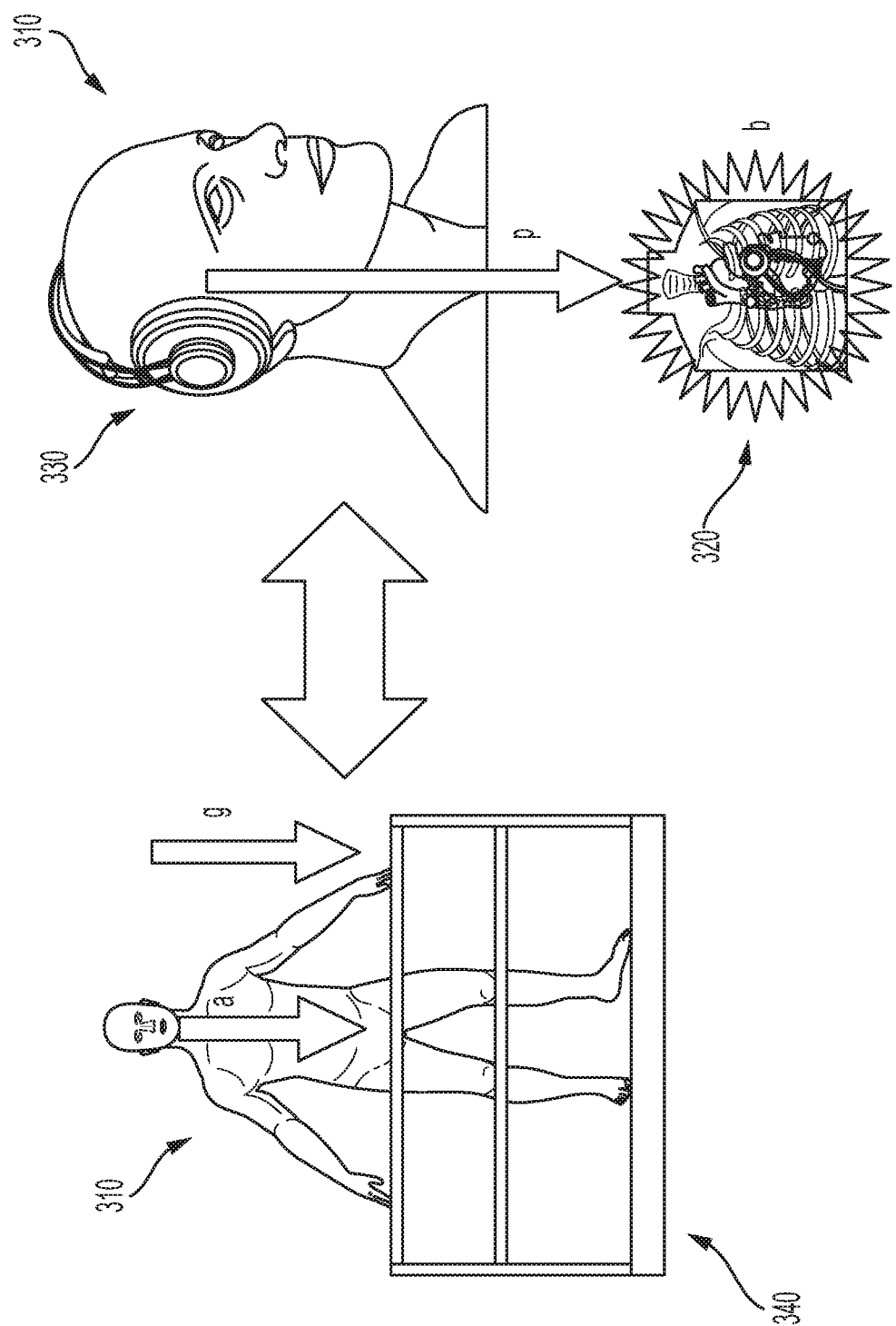

FIGS. 5A and 5B illustrate an example of a motion offsetting application of AIV according to certain embodiments. Similar to the examples discussed above, the orientation of a person or subject 310 can be sensed using sensors, such as a MEMS gyroscope and/or accelerometer(s). The sensor(s) can be mounted or worn on the subject's head, torso, or other body part(s). The sensors sense the orientation of the subject 310 (a vector) relative to gravity (g vector). An ecological auditory object 320 (e.g., a body sound, b, such as the sound of the subject's breath, heartbeat, or blood flow) is projected to offset a deviation of the a vector (orientation) from the g vector (gravity), and is provided to the subject 310 via headphones 330. In one example local body sounds (b) are sensed from the subject 310 and used as the auditory object 320; however, in other examples, other sounds can be used. The subject 310 hears the auditory object sound(s) at a projection vector p. Nominally, p is projected onto a virtual sphere (not shown) about the head of the subject 310. When the motion of the vehicle 340 causes the subject 310 to tilt relative to the gravity vector g, the sound(s) 320 are projected accordingly. For example, as shown in FIG. 5B, when the subject's attitude is canted relative to the g vector due to the motion of the vehicle 340, the body sounds b can be projected to provide a sense of motion offsetting the deviation of the a vector from the g vector. In some examples, the projection vector p may be derived by inverting the a vector.

In certain examples, the shape and symmetry of the projection sphere can be modified to carry additional information or enhance perceived deviations from g. For example, the angle of p may be exponentially exaggerated to enhance non-level attitude perception. The rate of change of the sphere radius (corresponding to linear translation) may be enhanced with synthesized Doppler shift to enhance awareness of velocity (e.g., of the vehicle 340 or the subject 310). In addition, in various examples the angle of p may be combined with supplementary sensors (e.g., a vehicle-mounted gyroscope or accelerometer) to enhance the offsetting of vehicle motion. In some examples, the ecological auditory object 320 may be collected using acoustic sensors; however, in other examples, the ecological auditory object 320 may be synthesized.

Certain embodiments described herein are directed to using enhanced auditorily induced vection to provide a common reference vector for a person or group of people. For example, in modified or ambiguous gravitational environments (e.g., in a spacecraft), an AIV gravity-simulator can be used to provide the persons (e.g., astronauts) with a directional sense of gravity, or common sense of the direction of "down." In other examples, AIV can be used to provide a group of individuals with a common reference, such as the direction of North or the location of a "home base" or other point of common interest, to assist the individuals in the group in maintaining their orientation relative to the common reference, even when it may be otherwise difficult to perceive the common reference vector or location.

Figure 6A:
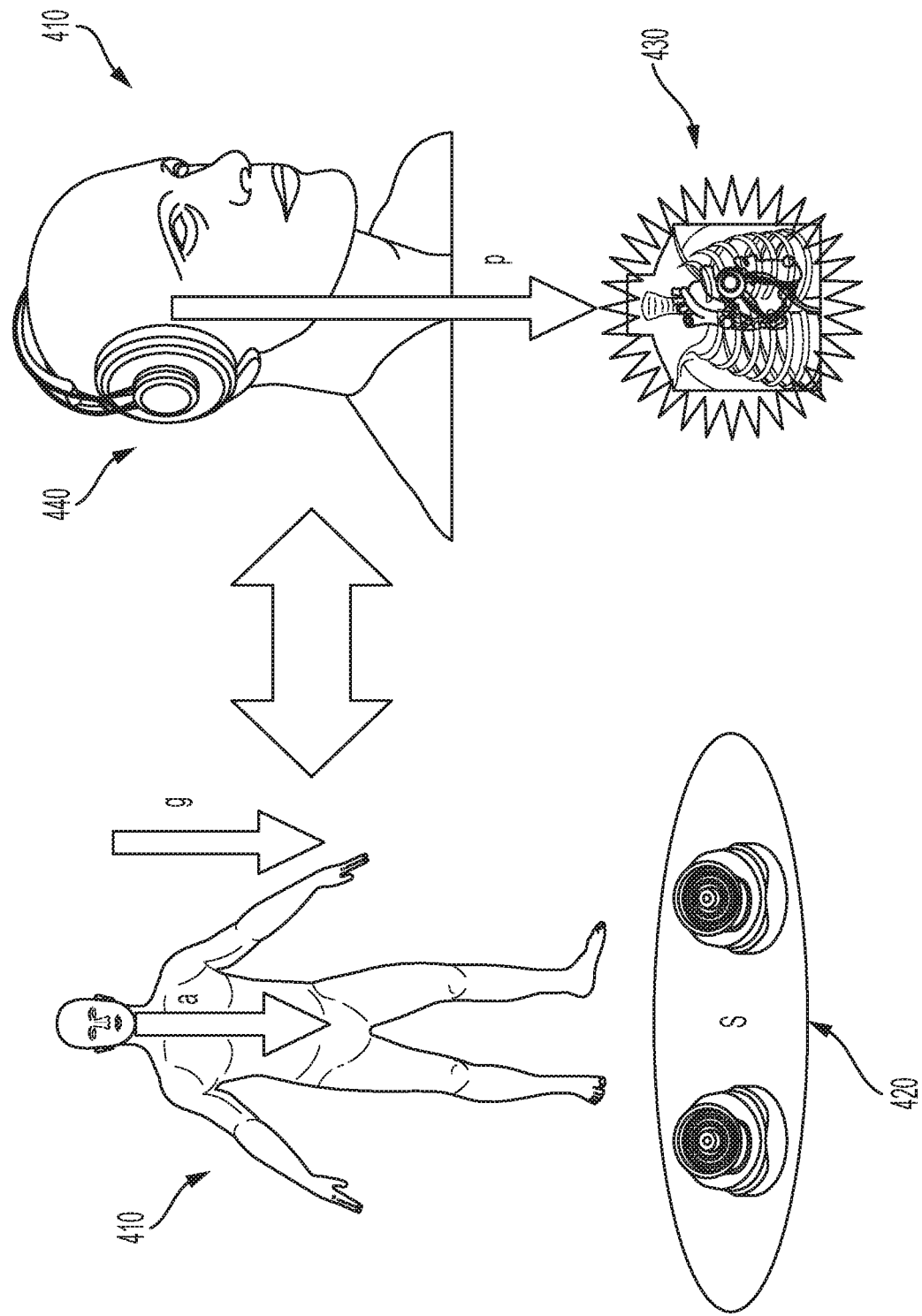
FIGS. 6A and 6B are diagrams conceptually illustrating the use of AIV to provide a sense of simulated gravity.
Figure 6B:
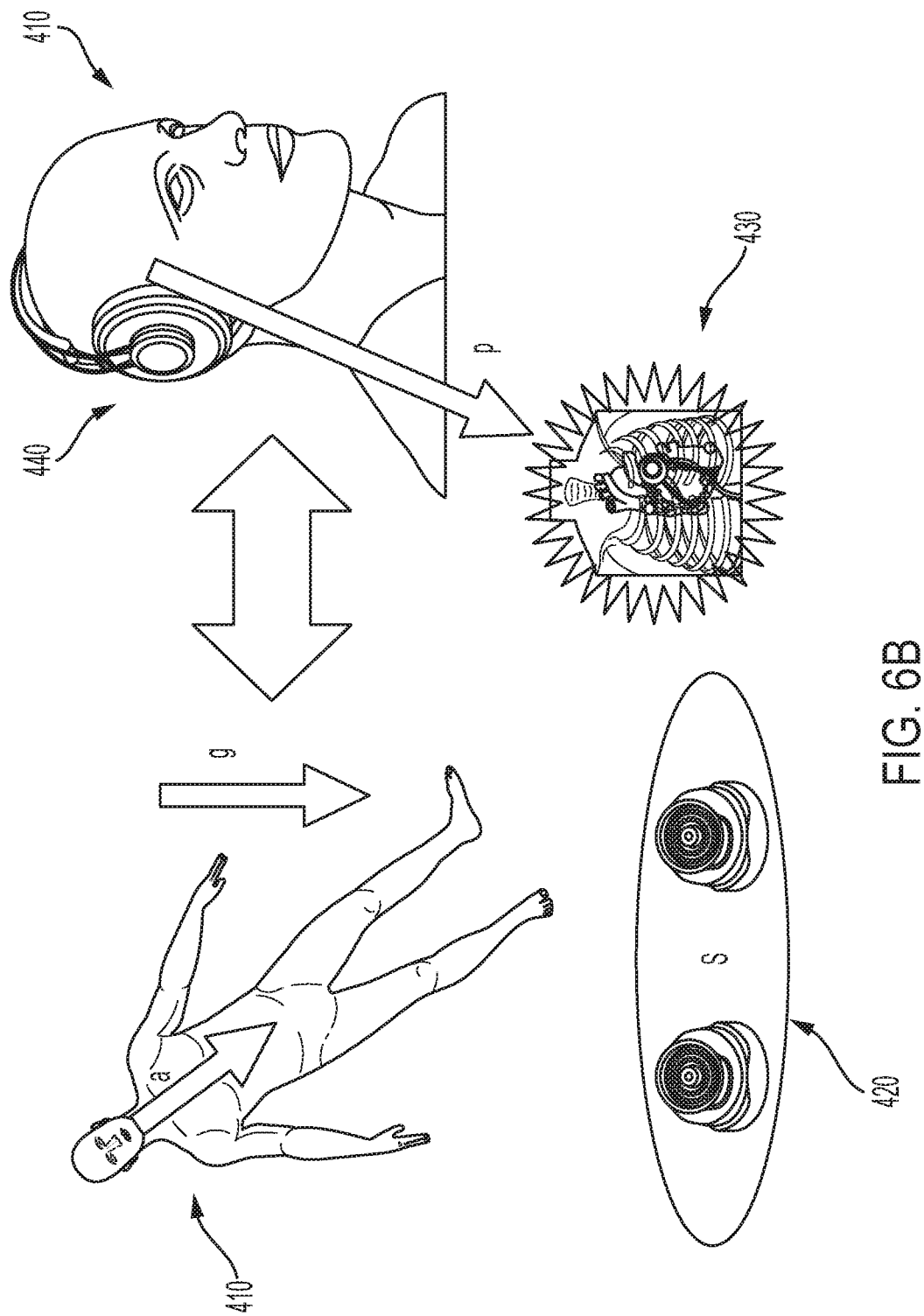

FIGS. 6A and 6B illustrate an example of using an AIV gravity-simulator according to certain embodiments described herein. In this example, the orientation of an operator 410 within a target reference frame is sensed using frame-referred sensors (e.g., video) or beacons (e.g., a VIVE virtual reality system manufactured by HTC of Taoyuan City, Taiwan, R.O.C.) 420, local to either the frame (e.g., a spacecraft) or the operator 410. In certain examples operator-local sensors 420 may be preferred for a compact and self-contained approach. In certain examples, the frame-referred sensors (s) 420 sense orientation (a vector) relative to simulated gravity (g vector) and transmit a to the operator 410. Similar to the examples discussed above, an ecological auditory object 430 (e.g., ambient spacecraft sounds or a body sound such as the operator's breath, heartbeat, or blood flow sound) is projected to indicate the target g vector (ambiguous, modified, or simulated gravity) to the operator 410 via headphones 440. In one example local body sounds (b) are sensed from the operator 410 and used as the auditory object 430; however, in other examples, other sounds can be used. The operator 410 hears the auditory object sound(s) at a projection vector p to convey a. Similar to the examples discussed above, nominally, p can be projected (using HRTFs as discussed above) onto a virtual sphere or other-shaped auditory volume (not shown) about the operator's head. When the operator's head attitude is canted relative to g, the sound(s) 430 are projected accordingly, as shown in FIG. 6B.

As discussed above, the shape and symmetry of the projection sphere (or virtual auditory space) can be modified to carry additional information or enhance perceived deviations from g. For example, the projection sphere radius may be made proportional to distance, e.g. to the "floor" of spacecraft, and represented by amplitude. The rate of change of the sphere radius (corresponding to linear translation) may be enhanced with synthesized Doppler shift to enhance awareness. In certain examples, the angle of p may be exponentially exaggerated to enhance non-level attitude perception. In addition, in various examples the angle of p may be combined with supplementary local sensors (e.g., a head-mounted gyroscope or accelerometer) to enhance operator attitude awareness. In some examples, the ecological auditory object 430 may be collected using acoustic sensors; however, in other examples, the ecological auditory object 430 may be synthesized.

Sonification is the mapping of data to sound in order to allow listeners to interpret it in an auditory manner. In certain embodiments, the same AIV system can also be used to sonify and project non-vection-related vector data into the reference frame of the operator. For example, when paired with suitable communications, location tracking, and absolute head-position sensing (e.g., digital compass), each soldier in a dismounted squad can be provided with an auditory object that indicates the centroid of the entire squad. If the squad needs to regroup, they can simply move toward the designated sound and will meet one another, irrespective of any fixed physical location. In addition, other tactical data (e.g. threats, friendly and adversary UAVs, etc.) can be overlaid onto the aural map with unique sounds to distinguish them and their key parameters (e.g., range, lethality, etc.).

Thus, aspects and embodiments described herein provide AIV-enhanced systems and methods to improve operator attitude awareness in a variety of different circumstances, applications, and environments. Various locally positioned and/or local-referenced sensors, such as MEMS gyroscopes, accelerometers, and the like, can be used to provide actual orientation or attitude measurements of the operator and/or of a remote object, such as a vehicle, tool, or other device. In certain examples, video or beacon technology can be used to sense operator attitude and/or the attitude of the remote object. Drift-controlled inertial sensors may also be used, alone or in combination with other sensors. As discussed above, certain applications may leverage one or more body sounds (e.g., heartbeat, breathing, etc.) of the operator as ecological auditory objects, while other examples may use environmental sounds or other synthesized sounds, such as beeps, tones, chirps, or band-limited noise. In various examples, predictive or other controller mechanisms may be leveraged to compensate for latency and overshoot. As discussed above, certain embodiments may leverage non-linearities to enhance AIV responses. For example, an exponential (or other non-linear) weighting can be applied to the positional error calculated from a comparison of the a vector relative to the g vector, such that the projection p changes in a non-linear manner to provide an enhanced sense of the positional error. This can be particularly useful in applications where it is desirable to maintain very close correlation with g (e.g., flying a remote vehicle with a very level attitude) as even a small deviation from the desired attitude can be projected as a large deviation, thereby enhancing the operator's perception of the error and encouraging the operator to take corrective action. The AIV-enhanced systems and methods disclosed herein may be compatible and interoperable with other sensory-modal interfaces (e.g., video, haptic, etc.). In addition, various examples may support performance-based validation, rather than simply subjective reporting of presence, AIV intensity, and AIV credibility or effectiveness.

Figure 7:
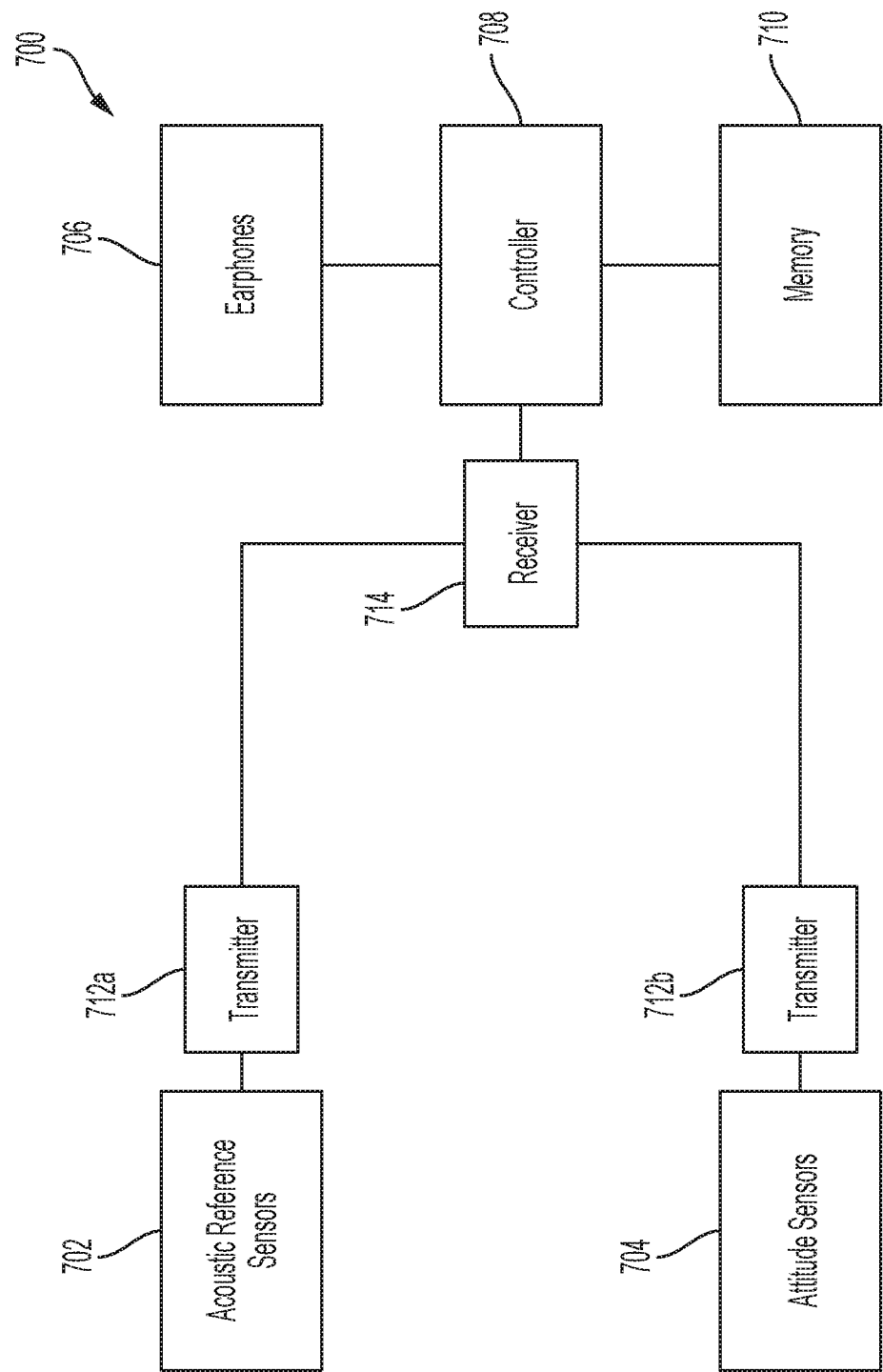
FIG. 7 is a block diagram of one example of the system architecture for an AIV system that may be used for any of the examples disclosed herein.

FIG. 7 is a block diagram of one example of a system architecture 700 that can be used to implement any of the examples of AIV-based systems and methods discussed above. The system architecture 700 includes acoustic reference sensors 702, attitude reference sensors 704, earphones 706, a controller 708, and a memory device 710. The controller 708 is configured to receive signals and/or data from the acoustic reference sensors 702 and the attitude sensors 704. In one embodiment, a transmitter 712 may transmit signals from the acoustic reference sensors 702 and the attitude sensors to a receiver 714 included in or connected to the controller 708. In some examples, the transmitter 712 may include a transmitter 712a configured to transmit signals from the acoustic reference sensors 702 and a transmitter 712b configured to transmit signals from the attitude sensors 704. The controller 708 may process the received signals and provide audio to a user via the earphones 706, as described above.

The acoustic reference sensors 702 may be any devices capable of detecting acoustic waveforms, such as microphones, vibration sensors, etc. The attitude sensors 704 may be any devices capable of detecting orientation, position, and/or movement. In some examples, the attitude sensors 704 may be devices such as gyroscopes, accelerometers, beacons, cameras, etc. In some embodiments, the acoustic reference sensors 704 and the attitude sensors 704 may each be a single sensor.

In various embodiments, the controller 708 may include one or more processors, specialized processors, or microcontrollers. The controller 708 may include specially-programmed, special-purpose hardware, for example, an application-specific integrated circuit (ASIC), or more generally designed hardware, such as a field programmable gate array (FPGA) or a processor. In one embodiment, the controller 708 is connected to the memory device 710. The memory device 710 may be, for example, a disk drive, memory, flash memory, embedded or on-chip memory, or other device for storing data. In one embodiment, the memory device 710 may be internal to the controller 708; however, in other embodiments, the memory device 710 may be external to the controller 708. In some examples, the memory device 710 may be one or more memory devices. In some embodiments, the controller 708 may be one or more controllers including one or more components such as one or more processors.

Figure 8:
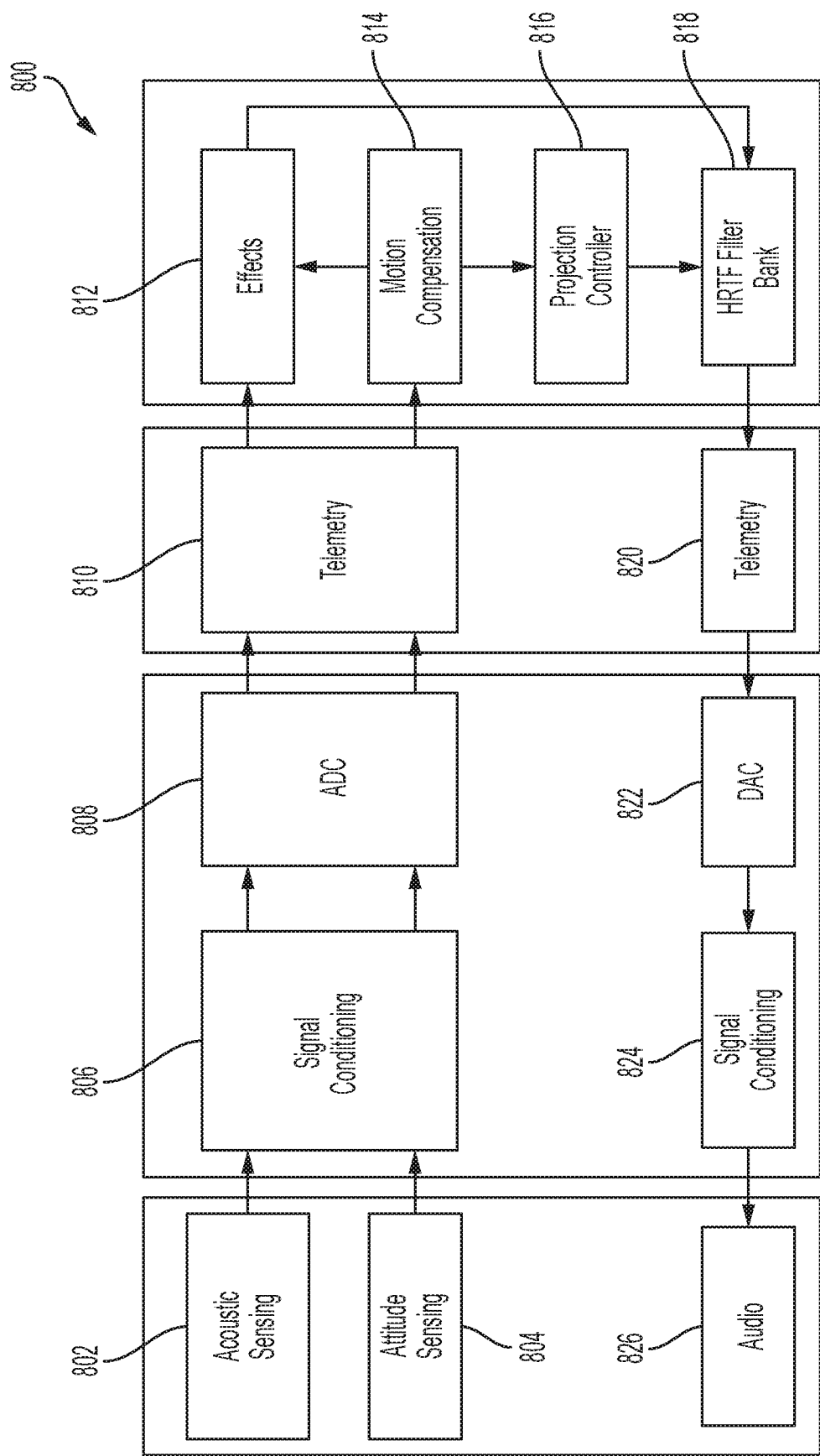
FIG. 8 is a flow diagram illustrating a process of using an AIV system for any of the examples disclosed herein.

FIG. 8 is a flow diagram illustrating a process 800 that can be used to implement any of the examples of AIV-based methods discussed above. In one embodiment, the process 800 may utilize the system architecture 700 to implement the various examples of AIV-based methods.

At block 802, the acoustic reference sensors 702 may sense and/or collect an ecological auditory object (e.g., a body sound, a vehicle sound, etc.). Similarly, at block 804, the attitude sensors 704 may sense and/or detect the orientation of a subject (e.g., vehicle, person, astronaut, etc.). As discussed above, in some embodiments, the attitude sensors 704 may sense the subject's orientation with respect to gravity; however, in other embodiments, the attitude sensors 704 may sense the subject's orientation with respect to a non-gravity reference.

In one embodiment, the ecological auditory object and the subject's orientation may be provided from the acoustic reference sensors 702 and the attitude sensors 704 as analog signals. At block 806, the analog signals may be conditioned (e.g., amplified, filtered, attenuated, etc.) before further processing and/or conversion. In one example, the analog signals provided from acoustic reference sensors 702 may be sensitive or susceptible to noise and may be conditioned (e.g., amplified) before further processing and/or conversion. The signal conditioning at block 806 may be performed using devices such as amplifiers, filters, attenuators, etc. In one example, the signal conditioning devices may be internal to the acoustic reference sensors 702 and the attitude sensors 704. In other examples, the signal conditioning devices may be external and in proximity to the acoustic reference sensors 702 and the attitude sensors 704.

At block 808, the conditioned analog signals may be converted to digital signals representing the ecological auditory object and the subject's orientation. The analog-to-digital conversion may be performed by one or more analog-to-digital converters (ADC). In one example, the ADC devices may be internal to the acoustic reference sensors 702 and the attitude sensors 704. In other examples, the ADC devices may be external and in proximity to the acoustic reference sensors 702 and the attitude sensors 704. In one example, the acoustic reference sensors 702 and the attitude sensors 704 may share an ADC device.

In some embodiments, the functionality provided by the signal conditioning devices at block 806 and the ADC devices at block 808 may be optional. For example, the subject's orientation may be provided from the attitude sensors 704 as a digital signal (e.g., video). Being that the signal representing the subject's orientation is already in digital form, conditioning and conversion of the signal may be unnecessary.

At block 810, a telemetry process provides the digital signals representing the ecological auditory object and the subject's orientation to the controller 708. In some embodiments, the telemetry process of block 810 may include telemetry devices such as transmitters, receivers, and/or transceivers. In one example, the telemetry devices may be configured to communicate over a wireless network connection to provide the digital signals representing the ecological auditory object and the subject's orientation to the controller 708. In some embodiments, the telemetry devices may be configured to communicate using wired, wireless, radio, acoustic, or optical communication protocols such as WiFi, Bluetooth, FrSky, DJI, etc.

In some examples, the telemetry devices may be included in the controller 708, the acoustic reference sensors 702, and the attitude sensors 704. For example, a wireless transmitter may be included in each of the acoustic reference sensors 702 and the attitude sensors 704 (e.g., transmitters 712a and 712b), and the controller 708 may include a receiver (e.g., receiver 714), or receivers, to receive the wireless signals transmitted from the acoustic reference sensors 702 and the attitude sensors 704. In other examples, the telemetry devices may be external and in proximity to each of the controller 708, the acoustic reference sensors 702, and the attitude sensors 704. In one example, a receiver may be configured to receive signals transmitted from a wireless transmitter on a remote vehicle or system. In other embodiments, the digital signals representing the ecological auditory object and the subject's orientation may be provided to the controller 708 over a wired connection (e.g., a cable, printed circuit board traces, etc.).

At block 812, the controller 708 may apply various effects to the digital signal representing the ecological auditory object. For example, the controller 708 may enhance the ecological auditory object signal by applying gain, Doppler shifts, etc. as needed. At block 814, the controller 708 may compensate for signal latency associated with the digital signals representing the ecological auditory object and the subject's orientation. In some examples, the controller 708 may utilize an adaptive or predictive filter to compensate for signal latency. For example, in one example the controller 708 may utilize a Kalman filter to compensate for signal latency.

At block 816, the controller 708 is configured to determine a desired source location for projection of the ecological auditory object collected by the acoustic reference sensors 702. The controller 708 may utilize the signals collected by the attitude sensors 704 and determine the desired source location based on the specific AIV application (i.e., telepresence, vestibular prosthesis, gravity simulation, etc.). At block 818, the controller 708 is configured to select a head-related transfer function (HRTF) based on the desired source location. In one example, the controller 708 may select an HRTF from an HRTF filter bank stored in memory (e.g., the memory device 710). The HRTF filter bank may include a plurality of HRTFs corresponding to a plurality of points in space around the subject. In some examples, the desired source location may correspond to a point in space located between two or more points having HRTFs in the HRTF filter bank, and the controller 708 may interpolate an HRTF for the desired source location using the HRTFs in the filter bank. The controller 708 may apply the selected (or interpolated) HRTF to the digital signal representing the ecological auditory object to project the ecological auditory object from the desired source location. In some examples, the controller 708 may select (or interpolate) a pair of HRTFs to produce a pair of digital signals representing the projected ecological auditory object; i.e., one for each ear of the user. In some examples, rather than projecting the ecological auditory object collected by the acoustic reference sensors 702, the controller 708 may be configured to project a pre-recorded or synthesized ecological auditory object.

At block 820, the digital signals representing the projected ecological auditory object are provided to the earphones 706. Similar to block 810, the telemetry process of block 820 may utilize telemetry devices such as transmitters, receivers, and/or transceivers. In one example, the telemetry devices may be configured to communicate over a wireless network connection to provide the digital signals representing the projected ecological auditory object to the earphones 706. In some embodiments, the telemetry devices of may be configured to communicate using communication protocols such as WiFi, Bluetooth, etc. as discussed above.

In some examples, the telemetry devices may be included in the controller 708 and the earphones 706. For example, a wireless transmitter may be included in controller 708, and the earphones 706 may include a receiver to receive the wireless signals transmitted from the controller 708. In other examples, the telemetry devices may be external and in proximity to each of the controller 708 and earphones 706. In other embodiments, the digital signals representing the projected ecological auditory object may be provided to the earphones 706 over a wired connection (e.g., a cable, printed circuit board traces, etc.).

At block 822, the digital signals may be converted to analog signals representing the projected ecological auditory object. The digital-to-analog conversion may be performed by a digital-to-analog converter (DAC). In one example, the DAC device may be internal to the earphones 706. In other examples, the DAC device may be external and in proximity to the earphones 706. At block 824, analog signals representing the projected ecological auditory object may be conditioned (e.g., amplified, filtered, attenuated, etc.) before being transmitted via the earphones 706. In one example, the analog signals may be conditioned (e.g., amplified) such that the analog signals are audible when transmitted via the earphones 706. In another example, the analog signals may be conditioned (e.g., filtered) to remove any undesired audible frequency content that could potentially impact or degrade AIV performance. Similar to block 806, the signal conditioning at block 824 may be performed using devices such as amplifiers, filters, attenuators, etc. In one example, the signal conditioning devices may be internal to the earphones 706. In other examples, the signal conditioning devices may be external and in proximity to the earphones 706.

At block 826, the conditioned analog signals representing the projected ecological auditory object may be provided to a user via the earphones 706. The user may hear the ecological auditory object projected from the desired source location to achieve a result of the specific AIV application.

In certain embodiments, in order to maximize system performance and minimize disorientation, the latency of the different system components (sensors, transceivers, signal processors, etc.) should be suitably controlled or compensated by the controller 708 to best coincide with true motion. This is easiest when all latencies are minimized, which may be achieved using sophisticated hardware and algorithm implementations. Among other techniques, certain examples may use precomputation of filter history terms and a speculative filtering technique (e.g., block 814) to reduce anticipated aggregate signal projection latency. Similarly, maximizing audio fidelity may be highly desirable critical. As discussed above, in certain examples custom HRTFs derived from the head and ear geometry of individual operators can be used to maximize audio quality; however, in other examples AIV can be effectively implemented using generic HRTFs. In addition, noise reduction and "situational gain control" mechanisms may be used (e.g., blocks 806 and 824) to improve operation in loud or noisy environments.

As described above, systems and methods directed to using AIV to provide a sense of direction or directional motion to enhance a person's attitude awareness are provided herein. By leveraging the low-cost availability of compact, sensitive micro-electro-mechanical systems (MEMS) transducers, dense, low-power processors and field-programmable gate arrays (FPGAs), a practical, wearable device can be provided that combines g (e.g., gravity) or other vectors with outputs from existing systems or other environmental features. The results can be mapped onto auditory objects with sufficiently low latency to produce AIV, enhancing a person's attitude awareness.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Thus, it is to be appreciated that embodiments of the methods and apparatuses discussed herein are not limited in application to the details of construction and the arrangement of components set forth in the foregoing description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or"

What is claimed is:

1. A method of using auditorily-induced vection (AIV) to provide a user with a sense of direction in a non-gravitational environment, the method comprising:
   determining a reference point within the environment;
   obtaining an auditory object associated with the user;
   determining an orientation of the user;
   projecting the auditory object based on the orientation of the user;
   providing the projected auditory object to the user to convey the user's orientation relative to the reference point; and
   determining a plurality of points in space about the user's head and a head-related transfer function (HRTF) corresponding to each of the plurality of points.

2. The method of claim 1, wherein determining the reference point includes determining a reference vector.

3. The method of claim 2, wherein determining the orientation of the user includes determining an orientation vector relative to the reference vector.

4. The method of claim 3, wherein projecting the auditory object based on the orientation of the user includes determining a projection source location based on the orientation vector.

5. The method of claim 4, wherein the projection source location is-a one of the plurality of points in space about the user's head.

6. The method of claim 4, wherein projecting the auditory object further includes applying the head-related transfer function (HRTF) corresponding to the projection source location to the auditory object.

7. The method of claim 6, wherein each HRTF represents a characterization of how the user hears sound from the corresponding projection source location.

8. The method of claim 6, wherein providing the projected auditory object to the user further includes indicating a deviation of the orientation vector from the reference vector.

9. The method of claim 8, further comprising modifying the projected auditory object to enhance the user's perception of the deviation of the orientation vector from the reference vector.

10. The method of claim 1, wherein the auditory object includes sound of one of the user's breath, heartbeat, and blood flow.

11. An auditorily-induced vection (AIV) system for providing a user with an enhanced sense of direction in a non-gravitational environment, the AIV system comprising:
    at least one acoustic sensor configured to sense an auditory object associated with the user;
    at least one attitude sensor configured to sense an orientation of the user;
    a controller configured to:
        receive the auditory object from the at least one acoustic sensor;
        receive the orientation of the user from the at least one attitude sensor;
        project the auditory object based on the orientation of the user and a reference point; and
        provide the projected auditory object to earphones to convey the user's orientation relative to the reference point; and
    a memory device coupled to the controller, the memory device configured to store a plurality of points in space about the user's head and a head-related transfer function (HRTF) corresponding to each of the plurality of points.

12. The system of claim 11, wherein the controller is further configured to determine a projection source location based on the orientation of the user and the reference point.

13. The system of claim 12, wherein in projecting the auditory object the controller is further configured to select a point from the plurality of points based on the projection source location and apply the corresponding HRTF to the auditory object.

14. The system of claim 12, wherein in projecting the auditory object the controller is further configured to select two or more points from the plurality of points based on the projection source location, interpolate an HRTF using the HRTFs corresponding to the two or more selected points, and apply the interpolated HRTF to the auditory object.

15. The system of claim 11, wherein the controller is further configured to modify the projected auditory object to enhance a non-level attitude perception.

16. The system of claim 15, wherein in modifying the projected auditory object the controller is further configured to make the projected auditory object louder to enhance the non-level attitude perception.

17. The system of claim 15, wherein in modifying the projected auditory object the controller is further configured to exaggerate a projection angle of the projected auditory object to enhance the non-level attitude perception.

18. The system of claim 11, wherein the controller is further configured to apply a Doppler shift to the auditory object to indicate a rate of change of the at least one user's orientation.

19. The system of claim 11, wherein the reference point is a location associated with a spacecraft.

* * * * *